(12) United States Patent
Manginell et al.

(10) Patent No.: US 7,118,712 B1
(45) Date of Patent: Oct. 10, 2006

(54) NON-PLANAR CHEMICAL PRECONCENTRATOR

(75) Inventors: Ronald P. Manginell, Albuquerque, NM (US); Douglas R. Adkins, Albuquerque, NM (US); Sara S. Sokolowski, Albuquerque, NM (US); Patrick R. Lewis, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 352 days.

(21) Appl. No.: 10/696,649

(22) Filed: Oct. 28, 2003

(51) Int. Cl.
*B01L 11/00* (2006.01)
(52) U.S. Cl. .................. 422/101; 96/108; 96/143; 210/510.1; 422/99; 422/100; 436/180
(58) Field of Classification Search .......... 422/99–101; 210/510.1; 96/108, 143; 436/180
See application file for complete search history.

(56) References Cited

U.S. PATENT DOCUMENTS

| | | | | |
|---|---|---|---|---|
| 5,194,154 | A | * | 3/1993 | Moyer et al. ............ 210/510.1 |
| 6,171,378 | B1 | * | 1/2001 | Manginell et al. ............ 96/143 |

* cited by examiner

*Primary Examiner*—Jill Warden
*Assistant Examiner*—Jyoti Nagpaul
(74) *Attorney, Agent, or Firm*—Kevin W. Bieg

(57) ABSTRACT

A non-planar chemical preconcentrator comprises a high-surface area, low mass, three-dimensional, flow-through sorption support structure that can be coated or packed with a sorptive material. The sorptive material can collect and concentrate a chemical analyte from a fluid stream and rapidly release it as a very narrow temporal plug for improved separations in a microanalytical system. The non-planar chemical preconcentrator retains most of the thermal and fabrication benefits of a planar preconcentrator, but has improved ruggedness and uptake, while reducing sorptive coating concerns and extending the range of collectible analytes.

52 Claims, 5 Drawing Sheets

Section A - A

Section A - A

Section A - A

Section B - B

Section A - A

Section B - B

NON-PLANAR CHEMICAL PRECONCENTRATOR

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to chemical analysis and, more particularly, to a non-planar chemical preconcentrator with a high internal surface area having a heatable sorptive coating or packing that can be used to selectively collect and concentrate one or more chemical species of interest from a fluid stream that can be rapidly released as a concentrated plug into a microanalytical chain for separation and detection.

BACKGROUND OF THE INVENTION

Portable, handheld microanalytical systems, which have been termed "chemical laboratories on a chip," are being developed to enable the rapid and sensitive detection of particular chemicals, including pollutants, high explosives, and chemical and biological warfare agents. These microanalytical systems should provide a high chemical selectivity to discriminate against potential background interferents and the ability to perform the chemical analysis on a short time scale with high sensitivity. In addition, low electrical power consumption is needed for prolonged field use.

Current gas-phase microanalytical systems typically comprise a gas chromatography column to separate the chemical species, or analyte, in a gas mixture and a detector to detect the separated species. Such microanalytical systems can also include a chemical preconcentrator. The chemical preconcentrator serves the important function of collecting and concentrating a chemical analyte on a sorptive material at the inlet of the microanalytical system. In particular, selective analyte preconcentration is an essential step for early-warning, trace chemical detection in real-world, high-consequence environments where a high background of potentially interfering compounds exists. The chemical preconcentrator can deliver an extremely sharp analyte plug to the downstream gas chromatograph by taking advantage of the rapid, efficient heating of the sorbed analyte with a low-heat capacity, low-loss microhotplate. The very narrow temporal plug improves separations, and therefore the signal-to-noise ratio and detectability of the particular chemical species of interest.

Previous microfabricated chemical preconcentrators have used a heated planar membrane suspended from a substrate as the microhotplate, wherein the sorptive material is disposed as a layer on a surface of the membrane to sorb the chemical species from a gas stream. See U.S. Pat. No. 6,171,378 to Manginell et al., which is incorporated herein by reference. The high thermal efficiency and extremely low heat capacity of the planar preconcentrator enables rapid thermal desorption of the chemical analyte with very low power consumption. However, analyte uptake on the sorptive layer is not optimum, due to sorptive materials limitations and the low collection area of the sorptive layer of the planar preconcentrator. Additionally, to allow for adequate contact of the analyte with the sorptive layer, intricate, post-process manifolds and/or flow lids may be required. Finally, the rapid desorption of the analyte when heated may cause the flow chamber to overpressure and rupture the thin suspended membrane, destroying the planar preconcentrator.

The present invention directly addresses the problems described above. Like the planar preconcentrator, the microscale non-planar chemical preconcentrator of the present invention can have a high thermal efficiency and a low heat capacity, enabling rapid desorption of the sorbed chemical analyte with low power consumption. However, the non-planar chemical preconcentrator uses a high-surface area, low mass, three-dimensional, flow-through support structure that can be coated or packed with a sorptive material. The high-surface area of the sorption support structure allows improved analyte collection and concentration, especially important for trace chemical detection. Furthermore, the flow-through structure allows pressure equalization across the thin heated membrane, preventing membrane rupture due to overpressure from analyte desorption and improving the mechanical ruggedness of the device. The non-planar chemical preconcentrator can be easily integrated with other microanalytical system components in a hybrid or monolithic fashion.

SUMMARY OF THE INVENTION

The present invention is directed to a non-planar chemical preconcentrator comprising a substrate having a suspended membrane formed thereon, at least one resistive heating element disposed on a surface of the suspended membrane, a sorption support structure disposed on the other surface of the suspended membrane, and a sorptive material disposed on the sorption support structure. The sorptive material acts to sorb and concentrate one or more chemical species of interest from a sample ambient or fluid stream over time and can rapidly release the sorbed chemical species in a concentrated plug upon rapid heating of the sorptive material using the resistive heating element.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 1A shows a top view of the cylindrical chemical preconcentrator. FIG. 1B shows a cross-sectional side view of the cylindrical chemical preconcentrator. FIG. 1C shows a bottom view of the cylindrical chemical preconcentrator.

FIG. 2A shows a top view of the channel chemical preconcentrator. FIG. 2B shows a cross-sectional side view of the channel chemical preconcentrator. FIG. 2C shows a cross-sectional top view of the channel chemical preconcentrator.

FIG. 3A shows a top view of the clamshell preconcentrator. FIG. 3B shows a cross-sectional end view of the clamshell chemical preconcentrator. FIG. 3C shows a cross-sectional end view of the clamshell chemical preconcentrator.

DETAILED DESCRIPTION OF THE INVENTION

The non-planar chemical preconcentrator of the present invention comprises a high-surface area, low mass, three-dimensional, flow-through sorption support structure that can be coated or packed with a sorptive material. The high-surface area sorption support can comprise a variety of flow-through structures, including concentric hollow cylinders, honeycomb structures, fins, posts, or the like. Described below are cylindrical, channel, and clamshell embodiments. Alternative high-surface area sorption support structures and non-planar preconcentrator configurations will be apparent to those skilled in the art.

Figure 1A:
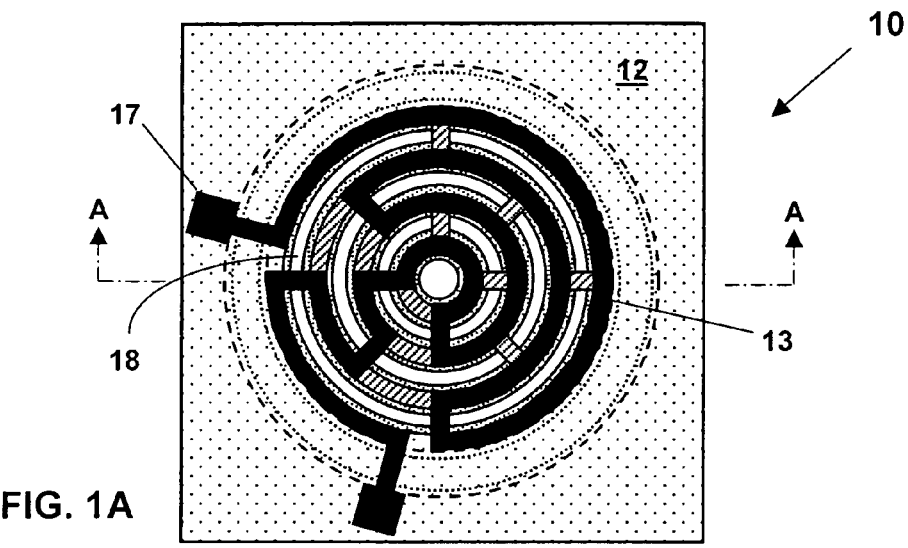
FIGS. 1A–1C show a cylindrical chemical preconcentrator comprising a plurality of concentric hollow cylinders as the sorption support structure.
Figure 1B:
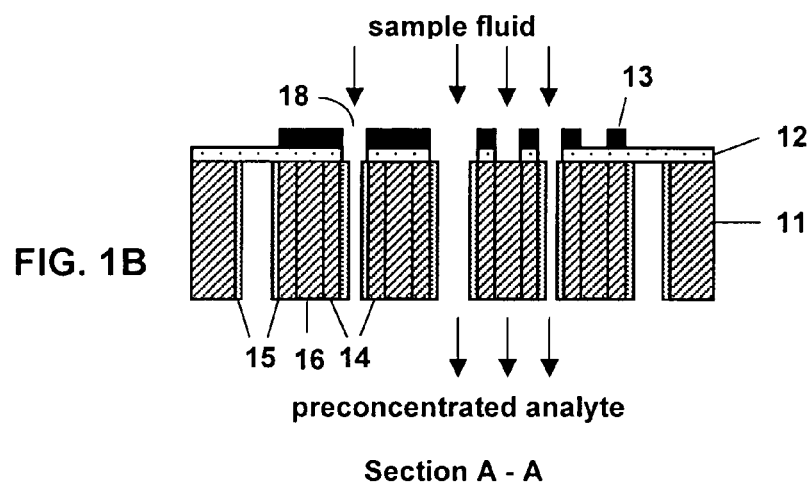
Figure 1C:
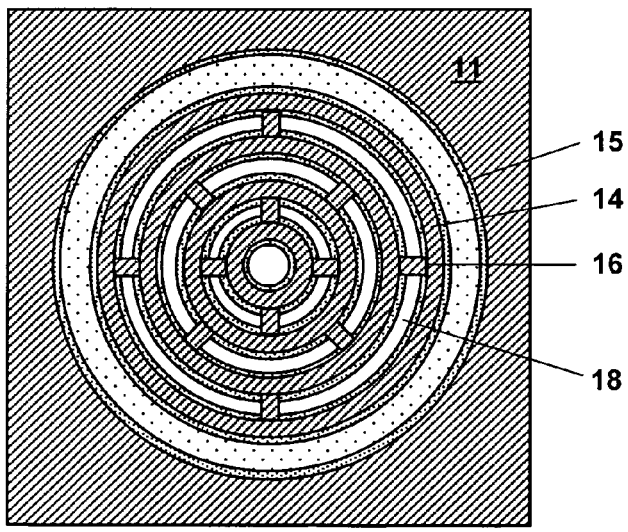

In FIGS. 1A–1C is shown a cylindrical embodiment of the non-planar chemical preconcentrator, comprising a plurality of concentric hollow cylinders as the sorption support structure. In FIG. 1B is shown a cross-sectional side view of the cylindrical chemical preconcentrator 10, comprising a substrate 11, a membrane 12 suspended from the substrate 11, a resistive heating element 13 disposed on a surface of the suspended membrane 12, and the sorption support structure 14 disposed on the other side of the membrane 12. To provide substantial surface area for adsorbent attachment, as well as to lend mechanical support on the inside edge of a membrane hole(s) 18, the sorption support structure 14 comprises a plurality of concentric hollow cylinders formed on the membrane 12, surrounding a central port. The sorption support structure 14 can be coated with a sorptive material 15. The sorptive material 15 acts to sorb or concentrate one or more chemical species of interest from an ambient or fluid sample flowing through the hole(s) 18 over time and can rapidly release the chemical species in a concentrated plug upon rapid heating of the sorptive material 15 using the resistive heating element 13. The cylindrical chemical preconcentrator 10 can further comprise mechanical support members 16 to interconnect the hollow cylinders of the sorption support structure 14.

The substrate 11 preferably comprises monocrystalline silicon, with a thickness of generally about 400–500 μm. Other substrates can also be used, including other semiconductor materials (e.g., gallium arsenide) or dielectric materials (e.g., a glass, crystalline quartz, fused silica, a plastic, or a ceramic).

The suspended membrane 12 is typically formed as a square (as shown) or circle with lateral dimensions of about one to a few millimeters. The suspended membrane 12 is supported on its edges by attachment to the substrate 11 (e.g., by adhesion of a deposited membrane-forming layer to the substrate 11 or to a sacrificial layer overlying the substrate 11). The suspended membrane 12 can be formed, for example, by depositing a film of the membrane material over a substrate and subsequently removing a portion of the substrate underlying the film using one of the methods described hereinafter. Similar to the planar chemical preconcentrator, low-pressure chemically vapor deposited (LPCVD) silicon nitride is a preferred membrane material due to its low stress, low thermal conductivity, and compatibility with integrated circuit (IC) processing steps. The membrane 12 is sufficiently thick (generally about 0.5–1 μm total thickness) for robustness as required for handling and to support the heating element 13 and the sorption support structure 14 and to withstand any thermally induced stresses.

In FIG. 1C is shown a bottom view of the cylindrical chemical preconcentrator 10. The sorption support structure 14 comprises a plurality of concentric hollow cylinders having sidewalls that provide a high-surface area support for the sorptive material 15 disposed thereon. For strength, the hollow cylinders can be joined together by radial struts as the mechanical support members 16. Preferably, the cylinders 14 and struts 16 comprise a high thermal conductivity material to allow the sorptive material to be uniformly and rapidly heated. Preferably, silicon cylinders and struts can be formed from the silicon substrate in a single masking and etching step. Additional mechanical support members (not shown) can further connect the sorption support structure 14 to the substrate 11 to provide additional mechanical ruggedness, although also providing a thermal conduction path to the substrate 11.

In addition to mechanically connecting the sorption support structure 14 to the substrate 11, the low thermal conductivity of the silicon nitride membrane 12 minimizes heat loss by conduction from the silicon sorption support structure 14, that is heated by the resistive heating element 13, outward to the supporting silicon substrate 11. Therefore, the thermal isolation characteristics of the planar preconcentrator can be achieved in the non-planar preconcentrator.

In FIG. 1A is shown a top view of the cylindrical chemical preconcentrator 10. The suspended membrane 12 can have at least one hole 18 formed therein to allow the fluid sample to flow through the membrane 12 and reach the sorptive material 15 coated on the sidewalls of the sorption support structure 14. The area of the hole(s) 18 in the suspended membrane 12 is preferably large to allow substantial fluid flow through the chemical preconcentrator 10. The hole(s) 18 can comprise annular openings in the membrane 12 between the concentric cylinders 14. The open, flow-through geometry also reduces membrane rupture encountered with the planar preconcentrator during excessive pressure fluctuations that sometimes occur during rapid heating and analyte desorption.

The sorbed chemical species can be rapidly released upon heating of the sorptive material 15 by the resistive heating element 13. The resistive heating element 13 can comprise a resistive conducting material. The resistive heating element 13 can be formed by depositing one or more layers of a metal or metal alloy over the membrane 12 on the opposite side from the sorption support structure 14 and patterning the layers to form the desired heater shape. The metal layers can include an adhesion layer (e.g., chromium) and a resistive layer (e.g., platinum, molybdenum, or tungsten). Alternatively, the resistive heating element 13 can be a doped semiconductor material, such as doped silicon. Preferably, the resistive layer has a suitably high temperature of coefficient of resistance (TCR of 2500–3000 ppm/° C.) to facilitate temperature measurement and control. Alternatively, a separate temperature sensor (not shown) can be used to control and measure the temperature during heating of the sorption support structure. The resistive heating element 13 can further include a plurality of bond pads 17 for electrical contact to a power source.

Preferably, the metal layer can be a folded circumferential structure patterned to follow the pattern of the concentric hollow cylinders 14 and the interconnecting mechanical struts 16 on the other side of the membrane 12. This folded circumferential pattern allows uniform heating of the sorption support structure 14, minimizes heat loss to the substrate 11, and provides unobstructed flow through the sorption support structure 14. Other arrangements of resistive heating elements, that substantially cover the intersected area of the suspended membrane and are thermally isolated from the substrate by their placement on the membrane, are possible.

The non-planar chemical preconcentrator can be formed by microfabrication methods known in the microelectromechanical systems (MEMS) and integrated circuits (IC) processing industries and described generally by Manginell et al. A fabrication method for the cylindrical chemical preconcentrator will be described. Similar fabrication methods can be used to form other embodiments of the non-planar chemical preconcentrator.

A thermal oxide etch stop layer (e.g., 0.5 μm thickness) can be grown and the silicon nitride membrane layer can be deposited by LPCVD on the front side of the silicon wafer.

The resistive heating element can be formed on the silicon nitride membrane layer by a lift-off process. A layer of photoresist can be spin-coated and patterned to expose the silicon nitride layer. Preferably, the resistive heating element comprises a folded circumferential structure. A metallic resistive heater layer is then deposited on the developed photoresist layer. The resistive heater layer can typically be a 0.35-μm-thick layer of platinum sputter-deposited on a 10-nm-thick chromium adhesion layer. The metal deposited over the remaining portions of the photoresist can be removed by lift-off of the photoresist, using acetone solvent. Similarly, a metallic bond pad layer (e.g., a 1-μm-thick layer of gold e-beam evaporated on a 10-nm-thick chromium adhesion layer) can be deposited and patterned on the silicon nitride membrane layer by a lift-off process to form the bond pads.

A hardmask layer (e.g., a 0.1-μm-thick layer of e-beam evaporated titanium) can be deposited and patterned on the frontside of the silicon wafer by a lift-off process. The titanium hardmask can be patterned to define the annular openings and the other portions of the silicon nitride membrane layer that are to be later removed.

A photoresist can be spun on the frontside to protect the hardmask and the resistive heating element during subsequent high-aspect-ratio etching (e.g., a Bosch etch) of the backside. A photoresist can be spun on the backside and patterned to provide a Bosch mask. The Bosch mask defines the sorption support structure and is preferably aligned to the folded circumferential pattern of the resistive heating element on the frontside of the silicon wafer. The exposed backside silicon can then be removed by Bosch etching, stopping on the oxide layer, to provide the sorption support structure. The frontside photoresist and the remaining backside photoresist can then be stripped. The exposed silicon nitride can be removed by dry etching in a $CF_4/O_2$ plasma through the frontside titanium hardmask to provide the annular openings in the membrane. The exposed oxide and the titanium hardmask can be removed with a buffered oxide etch comprising HF.

Following microfabrication of the preconcentrator, a sorptive material 15 can be applied to the sorption support structure 14. The sorptive material 15 can comprise a sol-gel oxide, a polymer, or a microporous material. For example, the microporous material can be porous silicon formed in the silicon support structure. Alternatively, the sorptive material 15 can be applied by spray coating, taking into account shadowing by the support structure. For example, the cylindrical preconcentrator 10 can be tilted or rotated during spraying to provide an adequate coating thickness on the interior portions of the concentric hollow cylinders 14. Alternatively, traditional dip coating, solvent coating, or vapor coating methods can also be used to apply the sorptive material 15. For example, a conformal nanoporous carbon coating, useful for the preconcentration of many toxic industrial chemicals, can be applied by laser ablation of a carbon target.

Alternative heater, sorptive coating, and sorption support structure configurations are possible. For example, the walls of the sorption support structure can be coated with a resistive film (e.g., platinum or indium-tin-oxide) and a sorptive coating can be applied to the resistive coating. Conductive metallizations (e.g., gold or aluminum) can be made to the front and backside to of the support structure to distribute current to the resistive-film-coated walls to heat and desorb analytes collected by the sorptive coating. Alternatively, electrical contacts can be made directly to the silicon cylinders and the cylinders themselves can be used as heaters and temperature sensors. Alternatively, the sorption support structure can be made of a metal, such as nickel, and be either inductively heated or resistively heated.

Figure 2A:
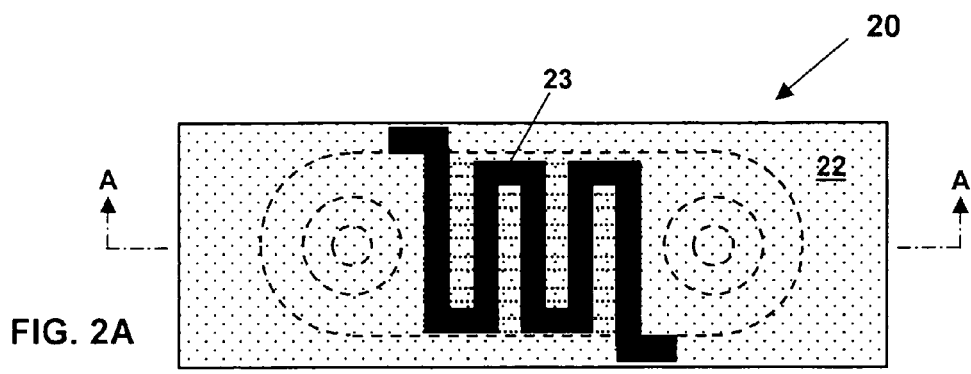
FIGS. 2A–2C show a channel chemical preconcentrator comprising a plurality of fins as the sorption support structure.
Figure 2B:
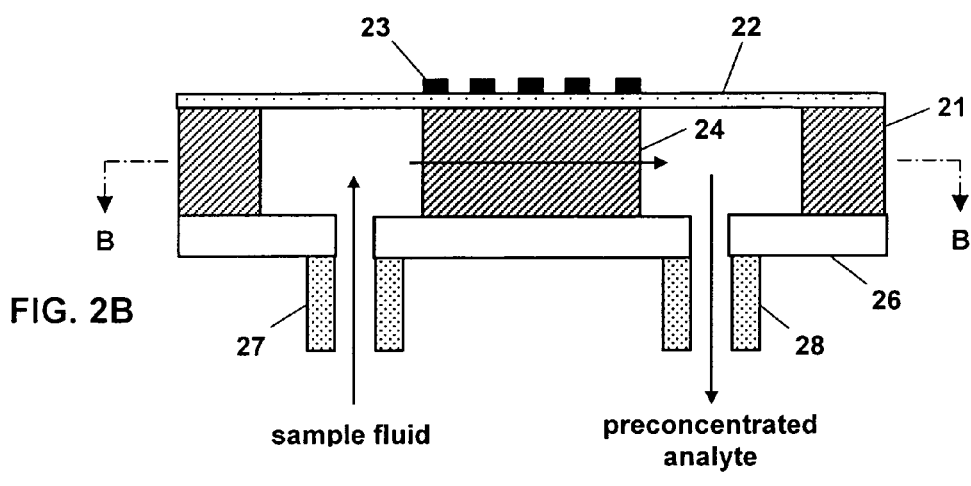
Figure 2C:
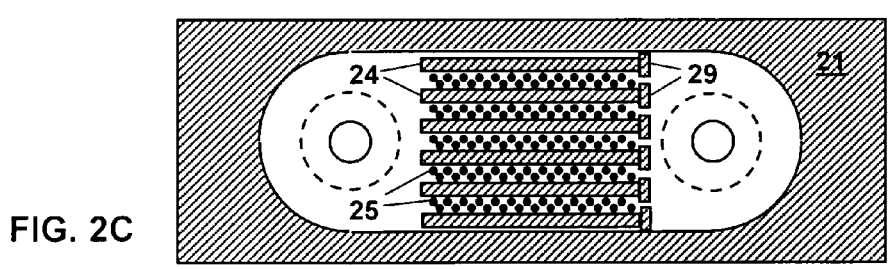

In FIGS. 2A–2C is shown a channel embodiment of the non-planar chemical preconcentrator, comprising a plurality of fins as the sorption support structure. FIG. 2B shows a cross-sectional side view of the channel chemical preconcentrator 20, comprising a substrate 21, a membrane 22 suspended from the substrate 21, a resistive heating element 23 disposed on a surface of the suspended membrane 22, and the sorption support structure 24 comprising the plurality of vertical fins disposed on the other surface of the membrane 22. The substrate 21 is preferably silicon and the fins of the sorption support structure 24 are preferably formed in the silicon substrate in a single masking and etching step. The height of the fins can be controlled by the etching process. The suspended membrane 22 is preferably low stress, low thermal conductivity silicon nitride to thermally isolate the fins 24 from the silicon substrate 21. The channel preconcentrator 20 can be fixtured with an attached glass lid 26 having an inlet capillary tube 27 for admitting a sample fluid and an outlet capillary tube 28 for providing a preconcentrated analyte containing the released chemical species of interest to the microanalytical chain. The capillary tubes 27 and 28 can be attached to the glass lid 26 by epoxy bonding or fused with a low-melting point glass solder.

In FIG. 2A is shown a top view of the channel preconcentrator 20. The resistive heating element 23 can be a circuitous or serpentine metal trace on the membrane 22 that substantially covers the area of the sorption support structure 24 connected to the other side of the membrane 22. Preferably, the circuitous metal trace can be patterned to follow the fin pattern of the sorption support structure 24 to provide optimal heating of the sorptive material.

In FIG. 2C is shown a cross-sectional top view of the channel preconcentrator 20. The sorption support structure 24 can be coated with a sorptive material, as described above for the cylindrical preconcentrator 10. Alternatively, the flow channels between the fins of the sorption support structure 24 can be packed with a particulate sorptive material 25 (as shown). Commercially available packing materials, such as PoropakQ, HayesepA, or Carboxen, can be retained in a polydimethylsiloxane (PDMS) binder that adheres to the sorption support structure 24. Alternatively, packing stops 29 can be microfabricated at the ends of the flow channels to retain the packing particles 25 in the flow channels.

The channel chemical preconcentrator 20 can be fabricated using methods similar to those described above for the cylindrical preconcentrator 10, except that it is not necessary to etch through the membrane layer. Alternative fabrication methods and material configurations are possible. For example, the channel preconcentrator 20 can be fabricated from a silicon-on-insulator (SOI) wafer wherein the membrane comprises the top silicon layer on the buried oxide layer of the SOI wafer and the sorption support structure can be Bosch etched in the silicon substrate. This configuration was the advantage that the capillary tubes can be anodically bonded to the silicon membrane. Although silicon has a higher thermal conductivity than silicon nitride, the heat loss from the silicon membrane to the substrate can be minimized by using a thin top silicon layer.

Figure 3A:
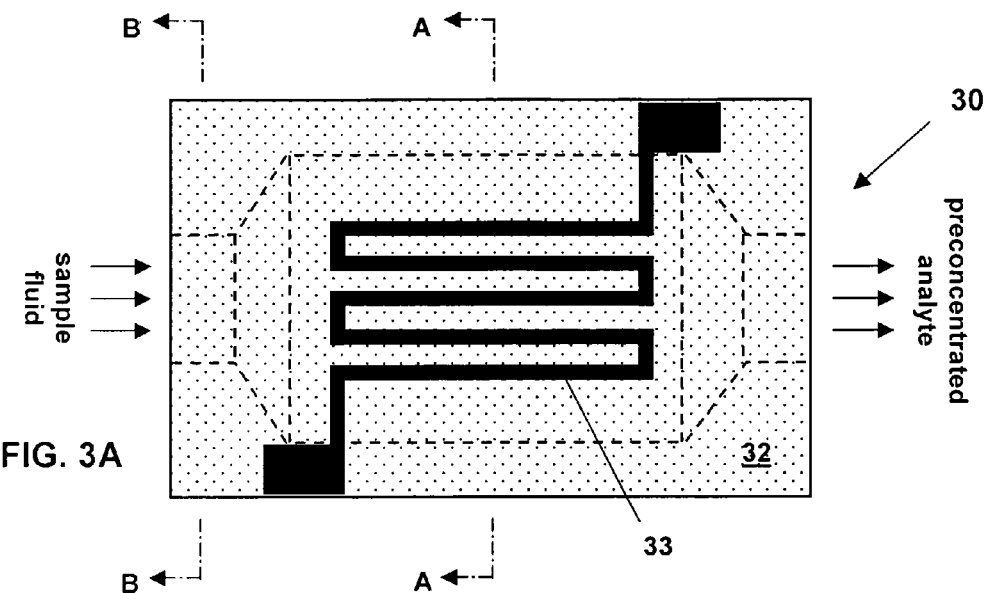
FIGS. 3A–3C show a clamshell chemical preconcentrator comprising opposed sorption support structures.
Figure 3B:
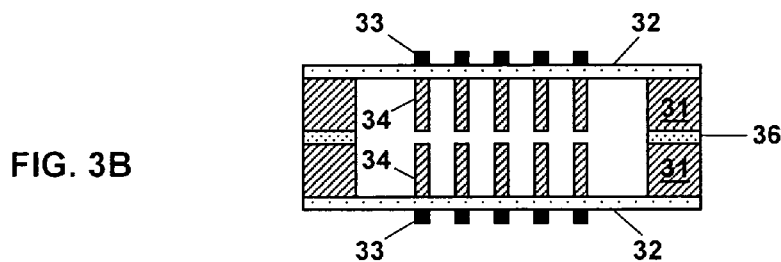
Figure 3C:
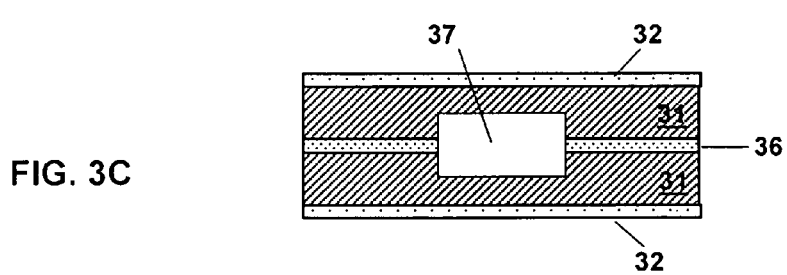

In FIGS. 3A–3C is a clamshell embodiment of the non-planar chemical preconcentrator, comprising opposed sorption support structures. In FIG. 3B is shown a cross-sectional end view of the clamshell chemical preconcentrator 30, comprising the opposed sorption support structures 34 wherein each support structure 34 is attached to a membrane 32 supported from separate substrates 31. The opposed substrates 31 can be bonded together by an epoxy or fusion bond 36. As with the channel preconcentrator 20, the sorption support structure 34 can comprise a plurality of fins with flow channels therebetween. As shown in FIG. 3A, separate resistive heating elements 33 can be a circuitous metal trace patterned on the outward side of the supported membranes 32 to follow the finned support structure 34 on inward side. The sorption support structure 34 can be either coated with a sorptive material, or the flow channels can be packed with a particulate sorptive material. As shown in FIG. 3C, inlet and outlet ports 37 can be etched in the silicon substrates 31. The clamshell preconcentrator 30 has a reduced heat capacity and thermal conductivity that enables optimum heating of the sorptive area, compared to the channel preconcentrator 20.

Performance of the Non-Planar Chemical Preconcentrator

The non-planar chemical preconcentrator retains most of the thermal and fabrication benefits of planar preconcentrator, but has improved ruggedness and uptake, while reducing coating concerns and extending the range of collectible analytes. The high-surface area support of the non-planar chemical preconcentrator significantly increases the useful adsorbent area, therefore improving analyte collection. Furthermore, with the non-planar preconcentrator, dead volume is reduced, due to the narrow channels through which the sample fluid must flow. This reduced dead volume improves collection and desorption relative to the planar chemical preconcentrator. However, because the mass of the sorption support structure is larger than that of the sorptive material layer of the planar preconcentrator, the time response of the non-planar preconcentrator is somewhat slower. However, this disadvantage is compensated for by improved reliability, analyte uptake, and dead volume.

Because of these advantages, the non-planar chemical preconcentrator has improved ability to collect analytes at lower concentrations and/or for shorter time periods than the prior planar preconcentrator. Therefore, trace analytes that cannot currently be collected with the planar preconcentrator, such as explosives due to their low volatility and concentration in the ambient, can be collected with the non-planar chemical preconcentrator. Use of the non-planar chemical preconcentrator in a microanalytical system can therefore lower the limit of detectability and increase the compactness of the system.

Figure 4A:
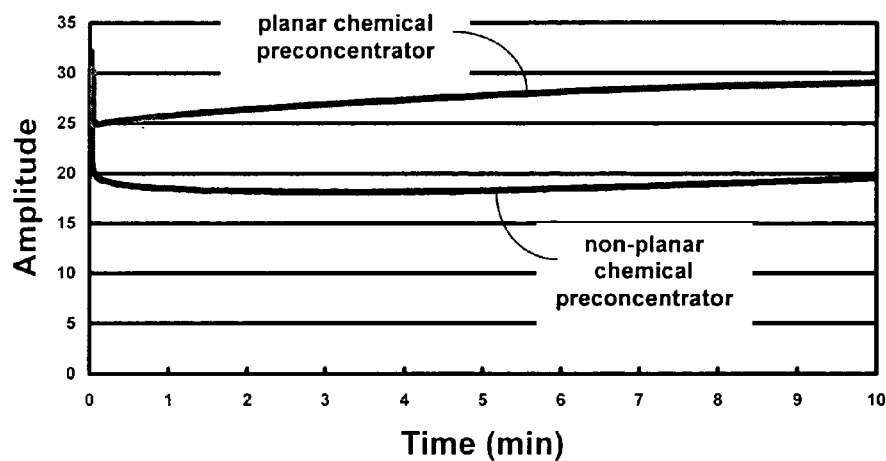
FIG. 4A shows the adsorption profiles for dimethyl methyl phosphonate (DMMP) of a planar chemical preconcentrator and a cylindrical chemical preconcentrator.

In FIG. 4A is shown the adsorption profiles for dimethyl methyl phosphonate (DMMP) for the planar chemical preconcentrator of Manginell et al., and the cylindrical chemical preconcentrator of the present invention. The figure shows the breakthrough of analyte downstream from the planar and non-planar preconcentrators as a function of time during the collection phase of the preconcentrator operation. The cylindrical preconcentrator demonstrates improved DMMP uptake over a long collection duration. The fluid flow through the cylindrical preconcentrator drops down further initially, indicating that the cylindrical preconcentrator is pulling more DMMP out of the fluid stream than the planar preconcentrator. Furthermore, the flow stays down longer and takes a longer time to return to baseline, indicating that the cylindrical preconcentrator doesn't saturate as quickly as the planar preconcentrator. The improved uptake is due to the larger adsorbent surface area of the cylindrical preconcentrator.

Figure 4B:
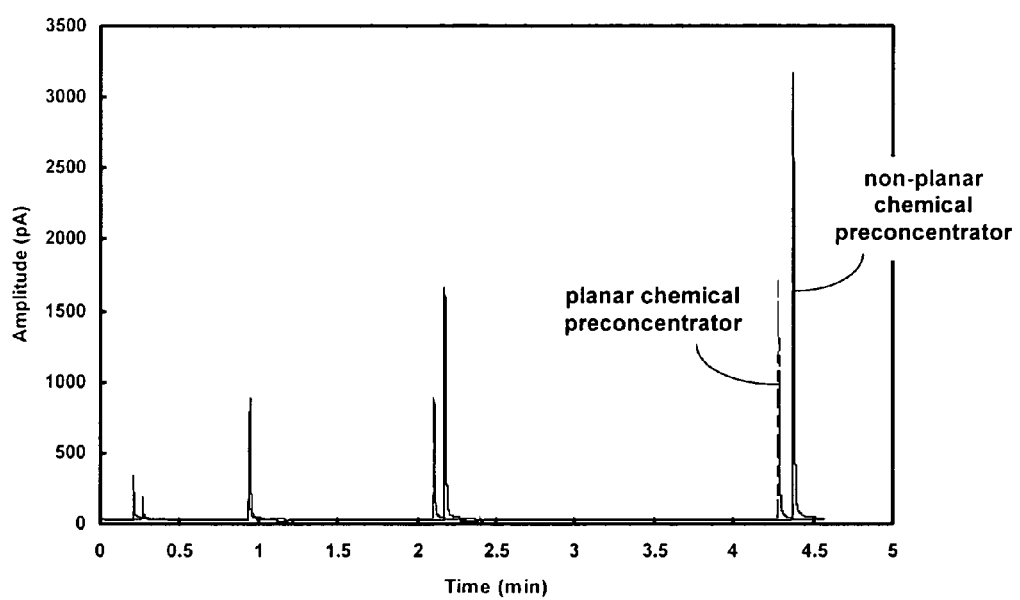
FIG. 4B shows the concentration enhancement of DMMP for various collection periods of the chemical preconcentrators.

In FIG. 4B is shown the desorption amplitudes of the DMMP for various collection periods for both the planar and the cylindrical chemical preconcentrators. The DMMP is released in a very narrow temporal plug due to the rapid heating of the sorbed DMMP in both preconcentrators. Even with collection periods of only a few minutes, the concentration enhancement of the cylindrical preconcentrator is improved by about twice over that of the planar preconcentrator.

Figure 5:
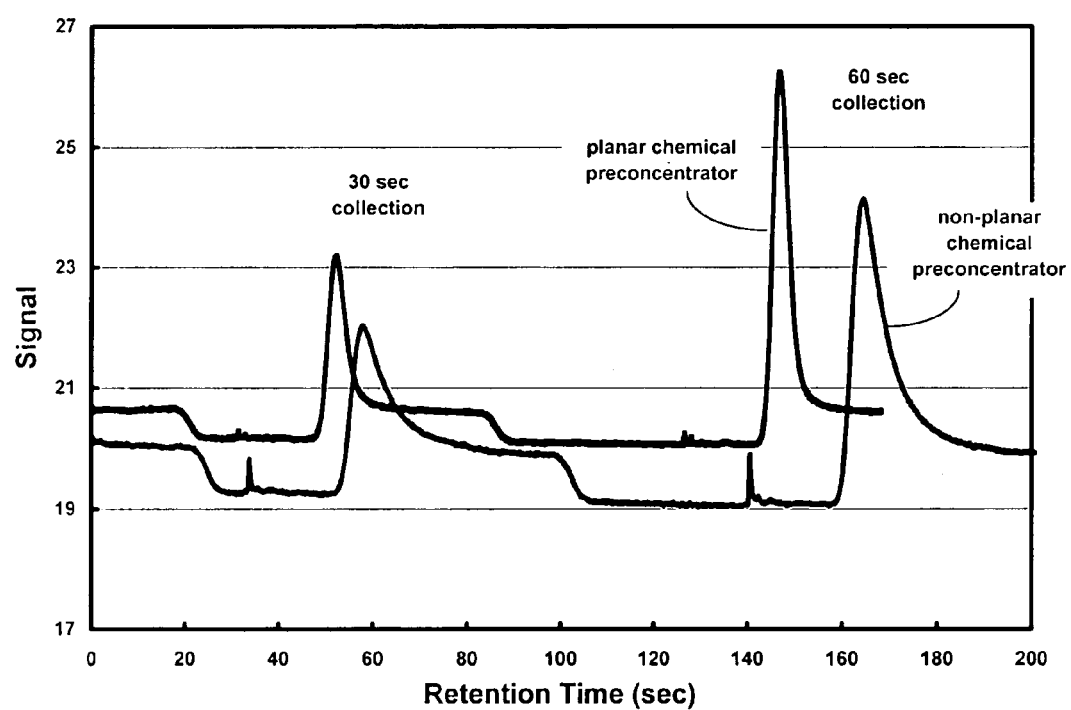
FIG. 5 shows the desorption profiles of the planar and cylindrical chemical preconcentrators after different sample collection periods.

The thermal isolation of the non-planar preconcentrator is comparable to the planar preconcentrator, enabling rapid thermal desorption of sorbed analytes. In FIG. 5 is shown the desorption profiles of the planar and cylindrical preconcentrators after sample collection periods of 30 sec. and 60 sec. The planar preconcentrator was ramped from 90 to 200° C. in 10 msec with a resistive heater power of 100 mW. The cylindrical preconcentrator could be ramped from 90 to 200° C. in 0.6–1 sec with a resistive heater power of 200–600 mW. Therefore, the cylindrical preconcentrator ramps somewhat more slowly, due to the added mass of the sorption support structure. However, this time response is still orders of magnitude better than can be achieved with conventional, macroscale preconcentrators that require many watts of heating power. Importantly, the desorption peak width of the microscale cylindrical chemical preconcentrator is comparable to that of the planar preconcentrator due to improved flow pattern and efficient heating of the sorption support structure.

The present invention has been described as a microscale, non-planar chemical preconcentrator. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A non-planar chemical preconcentrator, comprising:
   a substrate having a suspended membrane formed thereon with at least one hole formed in the suspended membrane for flow of a sample fluid therethrough,
   at least one resistive heating element disposed on a surface of the suspended membrane,
   a sorption support structure disposed on a surface of the membrane, and
   a sorptive material disposed on the sorption support structure to sorb and concentrate at least one chemical species from the sample fluid, with the chemical species being releasable from the sorptive material upon heating of the sorptive material by the at least one resistive heating element.

2. The non-planar chemical preconcentrator of claim 1, wherein the sorption support structure comprises a material selected from the group consisting of dielectrics and semiconductors.

3. The non-planar chemical preconcentrator of claim 1, wherein the sorption support structure comprises a plurality of concentric hollow cylinders.

4. The non-planar chemical preconcentrator of claim 1, wherein the suspended membrane is selected from the group consisting of semiconductors and dielectrics.

5. The non-planar chemical preconcentrator of claim 1, wherein the suspended membrane comprises a polymer layer.

6. The non-planar chemical preconcentrator of claim 1, wherein the at least one resistive heating element comprises a metal or metal alloy.

7. The non-planar chemical preconcentrator of claim 1, wherein the at least one resistive heating element comprises doped semiconductor material.

8. The non-planar chemical preconcentrator of claim 1, wherein the sorptive material comprises a microporous material.

9. The non-planar chemical preconcentrator of claim 8, wherein the sorptive material comprises porous silicon.

10. The non-planar chemical preconcentrator of claim 1, wherein the sorptive material comprises a sol-gel oxide.

11. The non-planar chemical preconcentrator of claim 1, wherein the sorptive material comprises a polymer.

12. The non-planar chemical preconcentrator of claim 1, wherein the sorptive material comprises a particulate material.

13. A non-planar chemical preconcentrator, comprising:
a substrate having a suspended membrane formed thereon,
at least one resistive heating element disposed on a surface of the suspended membrane,
a sorption support structure comprising a plurality of concentric hollow cylinders disposed on a surface of the membrane, and
a sorptive material disposed on the sorption support structure to sorb and concentrate at least one chemical species from a sample fluid, with the chemical species being releasable from the sorptive material upon heating of the sorptive material by the at least one resistive heating element.

14. The non-planar chemical preconcentrator of claim 13, wherein the sorption support structure comprises a material selected from the group consisting of dielectrics and semiconductors.

15. The non-planar chemical preconcentrator of claim 13, wherein the suspended membrane is selected from the group consisting of semiconductors and dielectrics.

16. The non-planar chemical preconcentrator of claim 13, wherein the suspended membrane comprises a polymer layer.

17. The non-planar chemical preconcentrator of claim 13, wherein the at least one resistive heating element comprises a metal, metal alloy, or doped semiconductor material.

18. The non-planar chemical preconcentrator of claim 13, wherein the sorptive material comprises a microporous material.

19. The non-planar chemical preconcentrator of claim 18, wherein the sorptive material comprises porous silicon.

20. The non-planar chemical preconcentrator of claim 13, wherein the sorptive material comprises a sol-gel oxide.

21. The non-planar chemical preconcentrator of claim 13, wherein the sorptive material comprises a polymer.

22. The non-planar chemical preconcentrator of claim 13, wherein the sorptive material comprises a particulate material.

23. A non-planar chemical preconcentrator, comprising:
a substrate having a suspended membrane formed thereon,
at least one resistive heating element disposed on a surface of the suspended membrane,
a sorption support structure comprising a plurality of fins disposed on a surface of the membrane, and
a sorptive material disposed on the sorption support structure to sorb and concentrate at least one chemical species from a sample fluid, with the chemical species being releasable from the sorptive material upon heating of the sorptive material by the at least one resistive heating element.

24. The non-planar chemical preconcentrator of claim 23, wherein the sorption support structure comprises a material selected from the group consisting of dielectrics and semiconductors.

25. The non-planar chemical preconcentrator of claim 23, wherein the suspended membrane is selected from the group consisting of semiconductors and dielectrics.

26. The non-planar chemical preconcentrator of claim 23, wherein the suspended membrane comprises a polymer layer.

27. The non-planar chemical preconcentrator of claim 23, wherein the at least one resistive heating element comprises a metal, metal alloy, or doped semiconductor material.

28. The non-planar chemical preconcentrator of claim 23, wherein the sorptive material comprises a microporous material.

29. The non-planar chemical preconcentrator of claim 28, wherein the sorptive material comprises porous silicon.

30. The chemical preconcentrator of claim 28, wherein the sorptive material comprises a sol-gel oxide.

31. The non-planar chemical preconcentrator of claim 28, wherein the sorptive material comprises a polymer.

32. The non-planar chemical preconcentrator of claim 28, wherein the sorptive material comprises a particulate material.

33. A non-planar chemical preconcentrator, comprising:
a substrate having a suspended membrane formed thereon,
at least one resistive heating element disposed on a surface of the suspended membrane,
a sorption support structure comprising a plurality of posts disposed on a surface of the membrane, and
a sorptive material disposed on the sorption support structure to sorb and concentrate at least one chemical species from a sample fluid, with the chemical species being releasable from the sorptive material upon heating of the sorptive material by the at least one resistive heating element.

34. The non-planar chemical preconcentrator of claim 33, wherein the sorption support structure comprises a material selected from the group consisting of dielectrics and semiconductors.

35. The non-planar chemical preconcentrator of claim 33, wherein the suspended membrane is selected from the group consisting of semiconductors and dielectrics.

36. The non-planar chemical preconcentrator of claim 33, wherein the suspended membrane comprises a polymer layer.

37. The non-planar chemical preconcentrator of claim 33, wherein the at least one resistive heating element comprises a metal, metal alloy, or doped semiconductor material.

38. The non-planar chemical preconcentrator of claim 33, wherein the sorptive material comprises a microporous material.

39. The non-planar chemical preconcentrator of claim 38, wherein the sorptive material comprises porous silicon.

40. The non-planar chemical preconcentrator of claim 33, wherein the sorptive material comprises a sol-gel oxide.

41. The non-planar chemical preconcentrator of claim 33, wherein the sorptive material comprises a polymer.

42. The non-planar chemical preconcentrator of claim 33, wherein the sorptive material comprises a particulate material.

43. A non-planar chemical preconcentrator, comprising:
a substrate having a suspended membrane formed thereon,
at least one resistive heating element disposed on a surface of the suspended membrane,
a sorption support structure comprising a honeycomb structure disposed on a surface of the membrane, and
a sorptive material disposed on the sorption support structure to sorb and concentrate at least one chemical species from a sample fluid, with the chemical species being releasable from the sorptive material upon heating of the sorptive material by the at least one resistive heating element.

44. The non-planar chemical preconcentrator of claim 43, wherein the sorption support structure comprises a material selected from the group consisting of dielectrics and semiconductors.

45. The non-planar chemical preconcentrator of claim 43, wherein the suspended membrane is selected from the group consisting of semiconductors and dielectrics.

46. The non-planar chemical preconcentrator of claim 43, wherein the suspended membrane comprises a polymer layer.

47. The non-planar chemical preconcentrator of claim 43, wherein the at least one resistive heating element comprises a metal, metal alloy, or doped semiconductor material.

48. The non-planar chemical preconcentrator of claim 43, wherein the sorptive material comprises a microporous material.

49. The non-planar chemical preconcentrator of claim 48, wherein the sorptive material comprises porous silicon.

50. The non-planar chemical preconcentrator of claim 43, wherein the sorptive material comprises a sol-gel oxide.

51. The non-planar chemical preconcentrator of claim 43, wherein the sorptive material comprises a polymer.

52. The non-planar chemical preconcentrator of claim 43, wherein the sorptive material comprises a particulate material.

* * * * *